United States Patent
Li et al.

(10) Patent No.: US 8,876,823 B2
(45) Date of Patent: Nov. 4, 2014

(54) STEEL PLATE FOR FUNNEL CHEST ORTHOPAEDIC SURGERY

(75) Inventors: Guoqing Li, Shanghai (CN); Ju Mei, Shanghai (CN); Deyu Zhu, Shanghai (CN)

(73) Assignee: Xinhua Hospital Affiliated to Shanghai Jiaotong University School of Medicine, Shanghai (CN)

( * ) Notice: Subject to any disclaimer, the term of this patent is extended or adjusted under 35 U.S.C. 154(b) by 359 days.

(21) Appl. No.: 13/259,785

(22) PCT Filed: May 26, 2010

(86) PCT No.: PCT/CN2010/073284
§ 371 (c)(1),
(2), (4) Date: Sep. 23, 2011

(87) PCT Pub. No.: WO2011/017962
PCT Pub. Date: Feb. 17, 2011

(65) Prior Publication Data
US 2012/0130371 A1 May 24, 2012

(30) Foreign Application Priority Data
Aug. 14, 2009 (CN) ...................... 2009 2 0207909 U

(51) Int. Cl.
*A61B 17/58* (2006.01)
*A61B 17/80* (2006.01)
(52) U.S. Cl.
CPC .......... *A61B 17/8076* (2013.01); *Y10S 606/905* (2013.01)
USPC ................................ 606/70; 606/71; 606/905
(58) Field of Classification Search
CPC .................................................. A61B 17/8061
USPC ........... 606/60, 62–64, 70, 71, 225, 280–299, 606/902–906; 411/537
See application file for complete search history.

(56) References Cited

U.S. PATENT DOCUMENTS 2,695,607 A * 11/1954 Hipps et al. ................... 600/210
3,799,169 A * 3/1974 Beroff et al. .................. 606/224
(Continued)

FOREIGN PATENT DOCUMENTS

| CN | 2657594 Y | 11/2004 |
| CN | 201154012 Y | 11/2008 |

(Continued)

OTHER PUBLICATIONS

International Search Report for PCT/CN2010/073284 dated Aug. 26, 2010.

*Primary Examiner* — Todd Manahan
*Assistant Examiner* — Eric S Gibson
(74) *Attorney, Agent, or Firm* — Banner & Witcoff, Ltd.

(57) ABSTRACT

A steel plate for funnel chest orthopaedic surgery includes a supporting plate (1), a fixing piece (2), a telescopic fixing piece (3), a guiding head (4) and screws (6). The supporting plate (1) is an elongate steel plate. One end of the supporting plate (1) is designed to be integrated with the fixing piece (2), and the other end is provided with a size-adjusting strap (5). The telescopic fixing piece (3) is an elongate steel plate with the same width as that of the supporting plate (1). One end of the telescopic fixing piece (3) is designed to be integrated with the fixing piece (2), and the other end is provided with a groove. The guiding head (4) is an elongate steel plate with the same width as that of the supporting plate (1). One end of the guiding head (4) is provided with a hook, and the other end is provided with a groove.

8 Claims, 5 Drawing Sheets

(56) References Cited

U.S. PATENT DOCUMENTS

| | | | | |
|---|---|---|---|---|
| 4,327,715 A | * | 5/1982 | Corvisier | 606/71 |
| 4,813,416 A | * | 3/1989 | Pollak et al. | 606/151 |
| 5,972,006 A | * | 10/1999 | Sciaino, Jr. | 606/151 |
| 6,024,759 A | * | 2/2000 | Nuss et al. | 606/237 |
| 6,918,910 B2 | * | 7/2005 | Smith et al. | 606/60 |
| 7,156,847 B2 | * | 1/2007 | Abramson | 606/60 |
| 8,348,949 B2 | * | 1/2013 | Butler et al. | 606/71 |
| 8,394,098 B2 | * | 3/2013 | Orbay et al. | 606/71 |
| 2004/0167521 A1 | * | 8/2004 | De Windt | 606/69 |
| 2006/0058786 A1 | * | 3/2006 | Kim et al. | 606/60 |
| 2006/0259141 A1 | * | 11/2006 | Roman et al. | 623/11.11 |
| 2008/0082101 A1 | * | 4/2008 | Reisberg | 606/60 |
| 2012/0041441 A1 | * | 2/2012 | Bernstein et al. | 606/74 |
| 2012/0130371 A1 | * | 5/2012 | Li et al. | 606/70 |
| 2013/0261625 A1 | * | 10/2013 | Koch et al. | 606/74 |

FOREIGN PATENT DOCUMENTS

| | | |
|---|---|---|
| CN | 201481536 U | 5/2010 |
| EP | 0583520 A1 | 2/1994 |
| WO | 2004028412 A1 | 4/2004 |
| WO | 2005055844 A1 | 6/2005 |

\* cited by examiner

STEEL PLATE FOR FUNNEL CHEST ORTHOPAEDIC SURGERY

TECHNICAL FIELD OF THE INVENTION

This present invention relates to surgical apparatus, particularly to a supporting steel plate for funnel chest orthopaedic surgery.

BACKGROUND OF THE INVENTION

Funnel chest is a congenital disease, which may affect the patient's respiratory and cardiopulmonary function. Therefore, it must be corrected. Currently, the most popular treatment of funnel chest is NUSS. At the beginning of the operation make a template according to thorax's size and shape and mold a steel plate according to above template. A thoracoscope is inserted through a small incision at the middle axillary line and the 7th intercostal space. Two incisions, with length about 2-3 cm and deep to the rib periosteum, are made along anterior axillary lines on the both sides. Along the outer space of the periosteum the separation toward the highest point of thoracic wall is made, the highest point and the lowest point of sternum are on the same line.

After that, the guiding device is interposed along the interstice from the right side, inserted to right thorax through the highest point of intercostal place, then, pass through mediastinum from the bottom of the rear of the sternum (the lowest point), and through the highest point of left thoracic chest, finally, stretch out the guiding device along the interstice on left thoracic wall and left incision on the profile thoracic wall. Mold the shape of the thoracic wall. The steel plate for funnel chest orthopaedic surgery is stretched out along the contrary route by the guiding device, and the steel plate is flipped, then the right fixing piece and the latch are fixed. NUSS has the advantages of fewer traumas, retaining thoracic flexibility and compliance, security, and easy operation compared to the other orthopedic surgeries. Whereas, its disadvantages are obvious and listed as follows:

1. The intercostal muscle is acted as the fulcrum of the steel plate, which may cause that the support is not sufficient and the plate is easy to sink, and affect the effect of orthopedic surgery sometimes tear the intercostal muscle and make the pain harder, particularly to the older and recurrent patients.
2. The curved steel plate may limit the normal development of thoracic wall, resulting in fracture of partial ribs frequently.
3. The fixing piece only has the function of anti-flip, but without the function of support, and its installation and demolition are difficult.
4. The effects of support and orthopedics are be impacted because that a interstice may be formed in result of the larger size of conductor apparatus than the steel plate, and severe soft tissue damage will be created for the overturn of steel plate, as well as the further expanded of tissue interstice.
5. The steel plate must be shaped during the operation, and may cause larger personal equation and technical difficulty.
6. The operation of eliciting the steel plate by conductor apparatus in the converse route is relatively complex.

There are some patents relating to funnel chest orthopedic surgery (refer to CN200720033095.2), whereas it also has the disadvantages above.

SUMMARY OF THE INVENTION

The objectives of this invention are to provide a steel plate for funnel chest orthopaedic surgery, simplify operative procedure and shorten operative time on the basis of NUSS.

To solve the above technical problem, the objectives of the present invention are achieved by the following technical methods: a steel plate for funnel chest orthopaedic surgery includes a supporting plate, a fixing piece, a telescopic fixing piece, a guiding head and screws, said supporting plate is an elongate steel plate, one end of the supporting plate is designed to be integrated with the fixing piece, and the other end is provided with a size-adjusting strap; said telescopic fixing piece is an elongate steel plate with the same width as that of the supporting plate, one end of the telescopic fixing piece is designed to be integrated with the fixing piece, and the other end is provided with a groove; said guiding head is an elongate steel plate with the same width as that of the supporting plate, one end of the guiding head is provided with a hook, and the other end is provided with a groove.

The chord length of said supporting plate is determined by the distance between the bilateral intercostal highest points corresponding to patient's lowest point of sternum, and the chord length is in the range of 9 cm to 27 cm.

The length, width and thickness of said size-adjusting strap are all smaller than that of said supporting plate.

The length of said telescopic fixing piece is less than that of said supporting plate, and the width and depth of groove of said telescopic fixing piece is separately the same as the width and thickness of said size-adjusting strap, the telescopic fixing piece and the size-adjusting strap are matched with each other.

The length of said guiding head is less than said supporting plate, and the width and depth of groove of said guiding head is the same as the width and thickness of said size-adjusting strap, the said guiding head and size-adjusting strap are matched with each other.

Said fixing piece is an elongate steel plate with a concave arcuate upper edge and a convex arcuate lower edge, and the two arcs have the same radian, the both ends of said fixing piece are separately to be arranged a via hole.

The sections with said groove of said size-adjusting strap, telescopic fixing piece and guiding head are separately to be arranged some via holes, the via hole's size and the distance between each two via holes of size-adjusting strap are all in accordance with those of said telescopic fixing piece and said guiding head.

The material of said steel plate is medical stainless steel or titanium alloy, to avoid the occurrence of allergic reaction.

Before operation, the chord length of supporting plate is determined by the distance of the bilateral intercostal highest points of corresponding to patient's lowest point of sternum. During operation, the supporting plate is connected to guiding head using the screws and inserted into the thoracic cavity. When it reaches the location for operation, the guiding head is removed in the converse route and the telescopic fixing piece is fixed on by screws. Hereto, the correction of funnel chest is completed.

The invention has the following positive effects:
1. The arcuate supporting point of the steel plate is located at the crossing of the highest point of bilateral ribs and corresponding intercostal muscle. Thereby, the sunk sternum could be jacked up to the normal level and intercostal muscle can be protected from tearing, so the best surgical results are be ensured.
2. The same size of steel and guiding head causes to less injuries to patient, and the steel plate does not have to be flipped, so that the difficulties of surgery are reduced. The subcutaneous tunnel is relatively short, so the steel plate could not move and would adapt perfectly to the tissue around after the operation.

3. The area of supporting point is extended and the distance of elevation of the sternum can be regulated by the fixing piece, and the arcuate lower edge of fixing piece has the function of supporting sternum and avoiding flipping.

4. The development of thorax will not be affected because the fixing piece and steel plate are not fixed on thoracic wall with the result of no restrictions of it, and the steel plate is limited in anterior thoracic wall, so that the operative effect can maintain for a longer period.

5. The chord length of said supporting plate is determined by the distance between the bilateral intercostal highest points corresponding to patient's lowest point of sternum and it will be produced by factory according to different specifications to avoid reprocessing operation and to improve the dimensional accuracy of steel plate.

6. According to regulating one side thickness of fixing piece, the relative side height of thoracic wall can be precisely regulated without bending steel plate, and the effect will be better for asymmetrical funnel chest patients.

7. One end of the fixing piece is fixing on steel plate, and the other end is connected with steel plate in socket type, ensuring installation and removing easy in surgery.

The invention will simplify the operation and shorten operative time on the basis of NUSS surgery, further ensure better results, improve the success rate, reduce the occurrence of complications and operative injury, ease patient's pain, save operation cost, and shorten the hospital stay.

LIST OF MAIN REFERENCE NUMBERS

Figure 1:
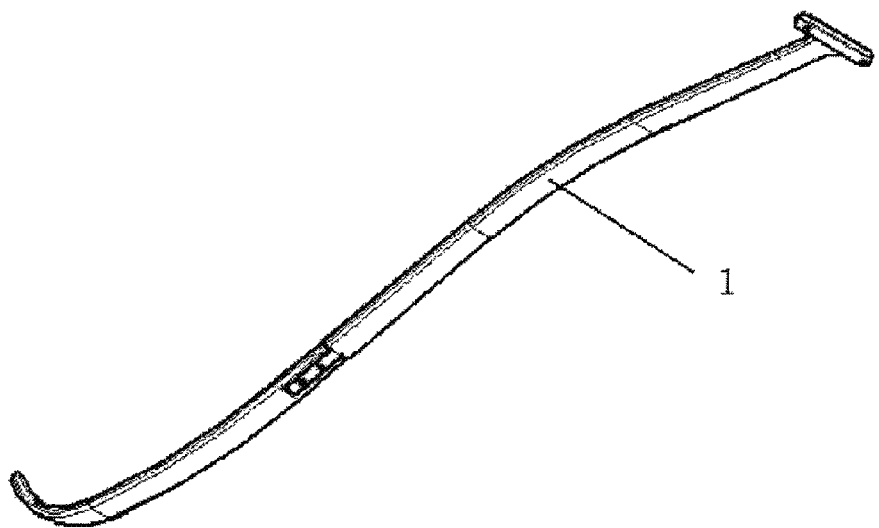
FIG. 1 is a schematic view of the supporting plate fixed with the guiding head.
Figure 2:
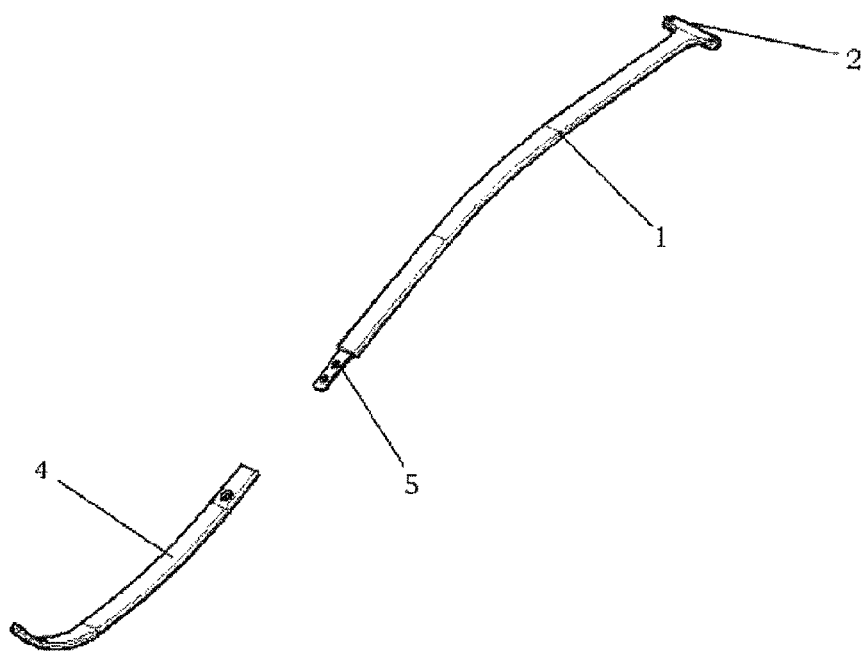
FIG. 2 is the exploded view of FIG. 1, shows the detachable relationship between supporting plate and guiding head.
Figure 3:
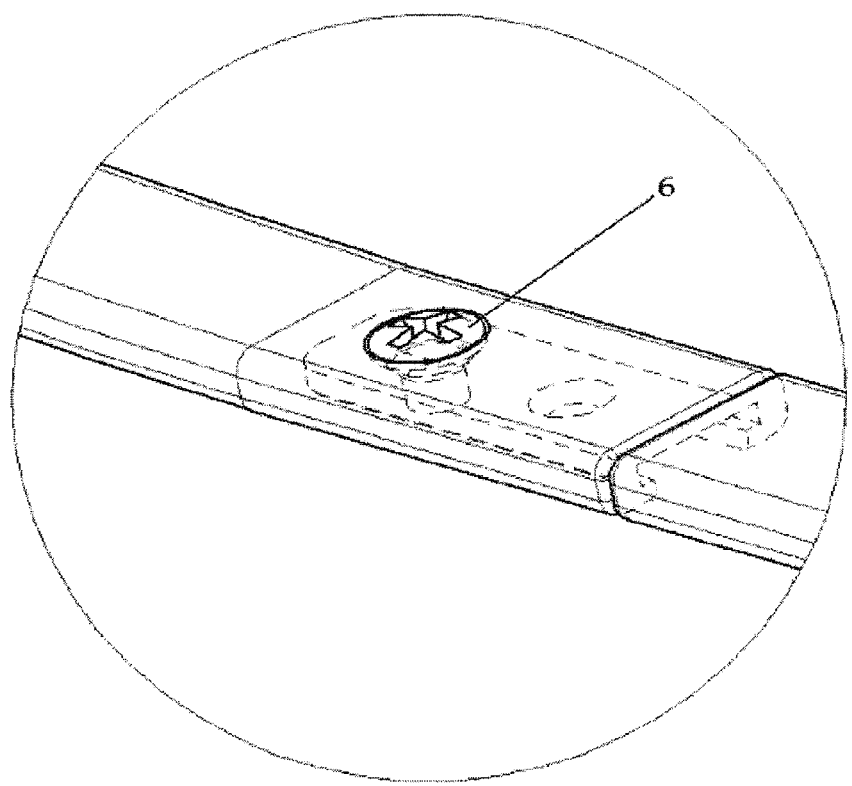
FIG. 3 is a detailed view of supporting plate and guiding head illustrating the detachable relationship between them.
Figure 4:
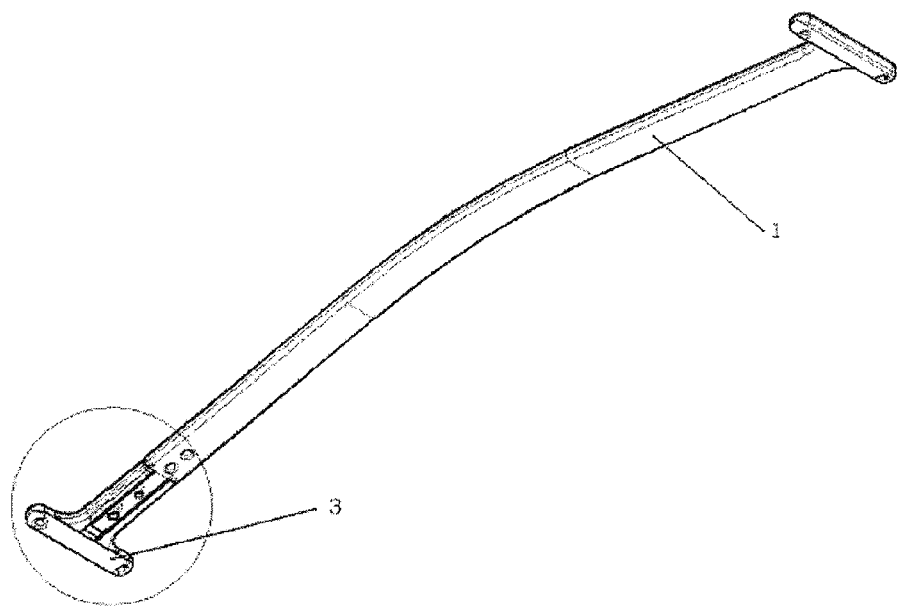
FIG. 4 is schematic view of the steel plate with a telescopic fixing piece.
Figure 5:
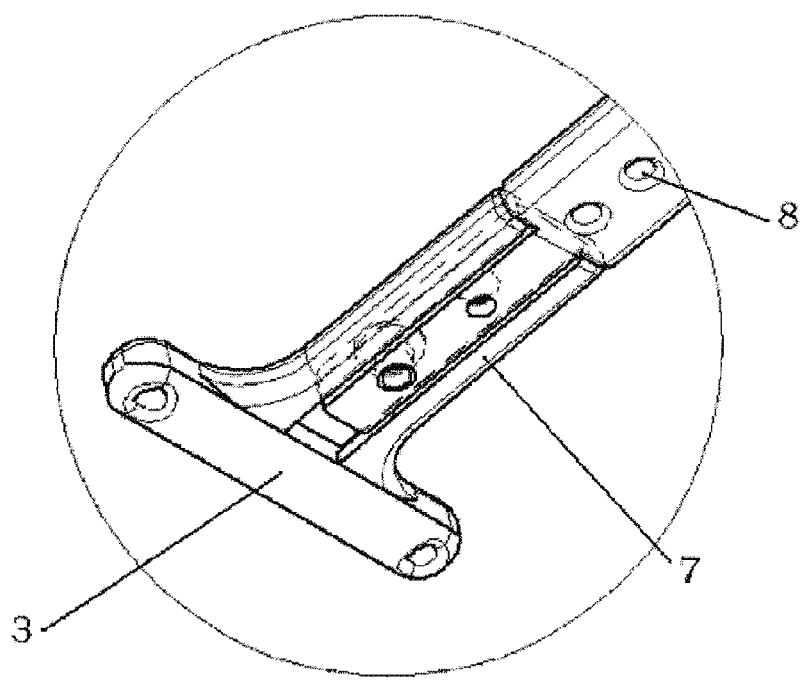
FIG. 5 is a detailed view of the steel plate with a telescopic fixing piece.
Figure 6:
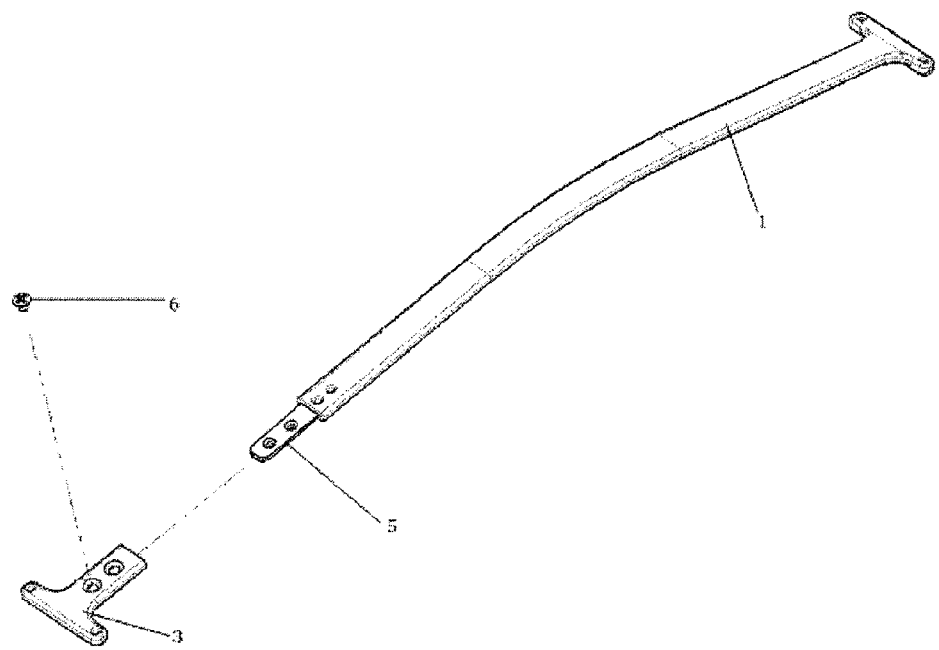
FIG. 6 is the exploded view of FIG. 4, shows the detachable relationship between supporting plate and telescopic fixing piece.
Figure 7:
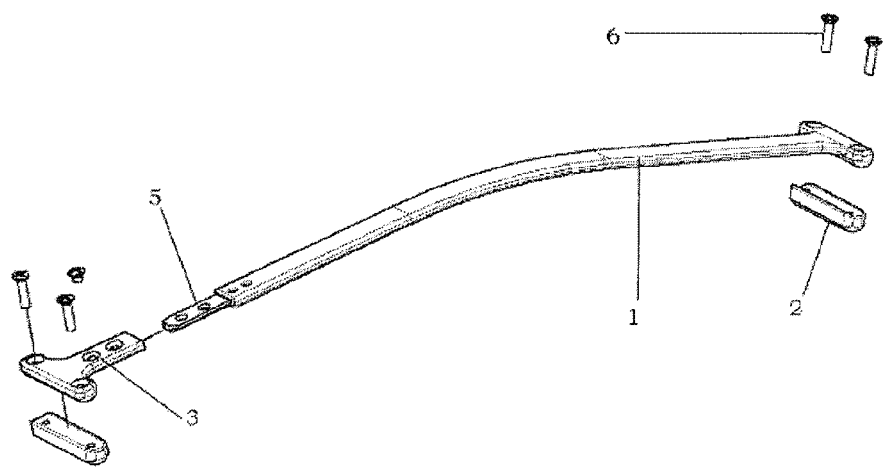
FIG. 7 is an exploded schematic view of the supporting plate fixed with the telescopic fixing piece.

| 1. Supporting plate | 2. Fixing piece |
| 3. Telescopic fixing piece | 4. Guiding head |
| 5. Size-adjusting strap | 6. Screws |
| 7. Groove | 8. Via holes |

DETAILED DESCRIPTION OF THE PREFERRED EMBODIMENT

Reference is made to the accompanying drawings in which is shown an illustrative embodiment of the invention from which its features and advantages will be apparent, whereas the principles and features of this invention may be employed in various and numerous embodiments without departing from the scope of the invention.

The steel plate for funnel chest orthopaedic surgery includes a supporting plate (1), a fixing piece (2), a telescopic fixing piece (3), a guiding head (4) and screws (6). Wherein said supporting plate (1) is an elongate steel plate with chord length in the range of 9 cm to 27 cm. One end of the supporting plate (1) is designed to be integrated with the fixing piece (2), and the other end is provided with a size-adjusting strap (5). The chord length of said supporting plate (1) is determined by the distance of the bilateral intercostal highest points corresponding to patient's lowest point of sternum. Said telescopic fixing piece (3) is an elongate steel plate with the same width as that of the supporting plate (1). One end of the telescopic fixing piece (3) is designed to be integrated with the fixing piece (2), and the other end is provided with a groove. The length of said telescopic fixing piece (3) is less than that of said supporting plate (1), and the width and depth of groove (7) of said telescopic fixing piece (3) is separately the same as the width and thickness of said size-adjusting strap (5). The telescopic fixing piece (3) and the size-adjusting strap (5) are matched with each other. Said guiding head (4) is an elongate steel plate with the same width as that of the supporting plate (1). One end of the guiding head (4) is provided with a hook, and the other end is provided with a groove. The length of said guiding head (4) is less than said supporting plate (1), and the width and depth of groove of said guiding head (4) is separately the same as the width and thickness of said size-adjusting strap (5). The said guiding head (4) and size-adjusting strap (5) are matched with each other.

The length, width and thickness of said size-adjusting strap (5) are all smaller than that of said supporting plate (1). Said fixing piece (2) is an elongate steel plate with a concave arcuate upper edge and a convex arcuate lower edge, and the two arcs have the same radian, the both ends of said fixing piece are separately to be arranged a via hole (8). The sections with said groove of said size-adjusting strap (5), telescopic fixing piece (8) and guiding head (4) are separately to be arranged some via holes (8), the via hole's size and the distance between each two via holes of size-adjusting strap (5) are all in accordance with those of said telescopic fixing piece (3) and guiding head (4). The material of said steel plate is medical stainless steel or titanium alloy, to avoid the occurrence of allergic reaction.

When used, according to the distance between the bilateral intercostal highest points corresponding to patient's lowest point of sternum, the chord length of supporting plate (1) is determined, and then the supporting plate (1) is connected to the guiding head (4) with screws (6). A thoracoscope is inserted through a small incision at the middle axillary line and the 8th/7th intercostal space. Two incisions, with length about 2 cm and deep to the rib periosteum, are made along anterior axillary lines on the both sides. Along the outer space of the periosteum the separation toward the highest point of thoracic wall is made, the highest point and the lowest point of sternum are on the same line. Next, the guiding device (not drawn in the drawings) is interposed along the interstice from the right side, inserted to right thorax through the highest point of intercostal place, then pass through mediastinum from the bottom of the rear of the sternum (the lowest point), and through the highest point of left thoracic chest, finally stretch out the guiding device along the interstice on left thoracic wall and left incision on the profile thoracic wall. Mold the shape of the thoracic wall. Then, the guiding device and the guiding head (4) of this invention are banded together by two-ply No. 7 operative suture. After that, the guiding head (4) is stretched out from the incision of right thoracic wall along the contrary route, and the junction of supporting plate (1) and guiding head (4) is exposed from patient's body. Remove screws (6) and the guiding head (4), replace them by the telescopic fixing piece (3) and connected with the supporting plate (1) by screws (6), and suture the incision.

The invention claimed is:

1. A steel plate for funnel chest orthopaedic surgery comprising:
   a supporting plate formed of an elongate steel plate, a first end of the supporting plate integrated with a first fixing piece so as to form a first T-shaped member, a size-adjusting strap extending outwardly from a second end of the supporting plate, the size-adjusting strap having a width that is less than a width of the supporting plate;
   a telescopic fixing piece formed of an elongate steel plate, a first end of the telescopic fixing piece having a first groove configured to receive the size-adjusting strap, the first end of the telescopic fixing piece configured to be attached to the strap with screws, a second end of the telescopic fixing piece integrated with a second fixing piece to form a second T-shaped member, the first end of the telescopic fixing piece having a width that is the same as the width of the supporting plate; and
   a guiding head formed of an elongate steel plate, a first end of the guiding head having a second groove configured to receive the size-adjusting strap, the first end of the guiding head configured to be attached to the strap with screws, a second end of the guiding head provided with a hook, a width of the first end of the guiding head being the same as the width of the supporting plate.

2. The steel plate of claim 1, wherein a chord length of said supporting plate is determined by a distance between bilateral intercostal highest points corresponding to a lowest point of a patient's sternum, and the chord length is in the range of 9 cm to 27 cm.

3. The steel plate of claim 1, wherein a length, width and thickness of said size-adjusting strap are all smaller than that of said supporting plate.

4. The steel plate of claim 1, wherein a length of said telescopic fixing piece is less than a length of said supporting plate, and a width and depth of the groove of said telescopic fixing piece are sized to receive said size-adjusting strap.

5. The steel plate of claim 1, wherein a length of said guiding head is less than a length of said supporting plate, and a width and depth of the groove of said guiding head are sized to receive said size-adjusting strap.

6. The steel plate of claim 1, wherein each fixing piece is an elongate steel plate with a first end and a second end, a concave arcuate upper edge and a convex arcuate lower edge, and the two arcuate edges have the same radian, the first and second ends of each fixing piece are separately to be arranged a via hole.

7. The steel plate of claim 1, wherein said size-adjusting strap, the groove of said telescopic fixing piece and the groove of said guiding head each include via holes, each via hole's size and a distance between each via hole of the size-adjusting strap are all in accordance with those of said telescopic fixing piece and said guiding head.

8. The steel plate of claim 1, wherein the material of said steel plate is medical stainless steel or titanium alloy.

* * * * *